United States Patent [19]

Alkemade et al.

[11] Patent Number: 5,759,554
[45] Date of Patent: Jun. 2, 1998

[54] IMMUNOSTIMULATORY BACTERIAL CELL WALL TRACTION

[75] Inventors: Stanley J. Alkemade, Arva, Canada; Thomas C. Buckley, Meath, Ireland; Graeme McRae, London, Canada

[73] Assignee: Vetrepharm, Inc., London, Canada

[21] Appl. No.: 352,452

[22] Filed: Dec. 9, 1994

Related U.S. Application Data

[63] Continuation of Ser. No. 11,655, Jan. 29, 1993, abandoned.

[51] Int. Cl.$^6$ .......................... A61K 45/00; A61K 45/05
[52] U.S. Cl. .......................... 424/282.1; 424/248.1; 424/279.1
[58] Field of Search .................. 424/282.1, 279.1, 424/248.1

[56] References Cited

U.S. PATENT DOCUMENTS

| | | | |
|---|---|---|---|
| 3,172,815 | 3/1965 | Fox et al. | 424/92 |
| 3,331,741 | 7/1967 | Anschel et al. | |
| 3,529,057 | 9/1970 | Tsuchiya | 424/92 |
| 4,010,257 | 3/1977 | Adlam et al. | |
| 4,013,788 | 3/1977 | Jolles et al. | |
| 4,036,953 | 7/1977 | Adam et al. | 424/92 |
| 4,069,314 | 1/1978 | Adlam et al. | |
| 4,110,434 | 8/1978 | Jolles et al. | |
| 4,340,586 | 7/1982 | Bekierkunst | |
| 4,503,048 | 3/1985 | Cantrell | |
| 4,504,473 | 3/1985 | Cantrell | |
| 4,505,903 | 3/1985 | Cantrell | |
| 4,663,311 | 5/1987 | Tenu et al. | |
| 4,744,984 | 5/1988 | Ragland et al. | 424/92 |

FOREIGN PATENT DOCUMENTS

| | | |
|---|---|---|
| 2 269 961 | 1/1976 | France. |
| 2 320 107 | 4/1977 | France. |
| 2662942 | 6/1990 | France. |
| WO 92/08488 | 5/1992 | WIPO. |

OTHER PUBLICATIONS

McLaughlin, C.A., et al., "Regression of Tumors in Guinea Pigs after Treatment with Synthetic Muramyl Dipeptides and Trehalose Dimycolate", *Science*, vol. 208, pp. 415–416 (Apr. 25, 1980).

Charley, B., et al., "In vitro effects of lipopolysaccharides and mycrobacterial cell wall components on swine alveolar macrophages," *Research in Veterinary Science*, vol. 34, pp. 212–217 (1983).

Lederer, E., "Synthetic Immunostimulants Derived from the Bacterial Cell Wall," *Journal of Medicinal Chemistry*, vol. 23, No. 8, pp. 819–821 (Aug. 1980).

Chess, L., M.D., et al., "Immunologic Effects of BCG in Patients with Malignant Melanoma: Specific Evidence for Stimulation of the Secondary Immune Response," *Journal of the National Cancer Institute*, vol. 51, No. 1, pp. 57–65 (Jul. 1973).

Bast, R.C., Jr., M.D., et al., "BCG and Cancer," *The New England Journal of Medicine*, vol. 29, No. 25, pp. 1413–1420 (Jun. 20, 1974).

Chedid, L., et al., "Enhancement of nonspecific immunity to Klebsiella pneumoniae infection by a synthetic immunoadjuvant (N–acetylmuramyl–L–alanyl–D–isoglutamine) and several analogs," *Proc. Natl. Acad. Sci.*, vol. 74, pp. 2089–2093 (1977).

Lopez–Berestein, G., et al., "The Activation of Human Monocytes by Liposome–encapsulated Muramyl Dipeptide Analogues," *The Journal of Immunology*, vol. 130, No. 4, pp. 1500–1502 (Apr. 1983).

Chedid, L., et al., "Protective Effect of Delipidated Mycobacterial Cells and Purified Cell Walls against Ehrlich Carcinoma and a Syngeneic Lymphoid Leukemia in Mice," *Cancer Research*, vol. 33, pp. 2187–2195 (Sep. 1973).

Meyer, T.J., et al., "Biologically Active Components from Mycrobacterial Cell Walls. II. Suppression and Regression of Strain–2 Guinea Pig Hepatoma," *Journal of the National Cancer Institute*, vol. 52, No. 1, pp. 103–111 (Jan. 1974).

Mathe, G., et al., "An Experimental Screening for 'Systemic Adjuvants of Immunity' Applicable in Cancer Immunotherapy," *Cancer Research*, vol. 33, pp. 1987–1997 (Sep. 1973).

Green, H.H., "Weybridge P.P.D. Tuberculins," *The Veterinary Journal* (British Veterinary Journal), vol. 102, pp. 267–278 (1946).

Edelman, "Vaccine Adjuvants," *Reviews of Infectious Diseases*, vol. 2, No. 3, pp. 370–383 (1980).

Taniyama, et al., "Adjuvant Activity of Mycobacterial Fractions," *Japan, J. Microbiol.*, vol. 18, No. 6, pp. 415–426 (1974).

Bernstein, et al., "Enhancement of the immune response elicited with foot–and–mouth disease virus vaccines by an extract by the Mycobacterium sp. wall," *Vaccine*, vol. 9, pp. 883–888 (1991).

Azuma et al., *Japan J. Micobiol.*, vol. 15, No. 2, pp. 193–197 (1971).

Ko et al. Medical Micro & Immunol. 170(1):1–9, 1981 Abstract only.

Azuma et al., Jap. J. Microbiol. 15(2):193–197, 1971.
Edelmin et al. Rev. Infect. Dis., 2(3):370–83, 1980.
Taniyama et al., Jpn. J. Microbiol., 18(6):415–26, 1974.
Berinstein et al., Vaccine, 9:883–888, 1991.
Chedid et al. Cancer Research 33:2187–2195, 1973.

*Primary Examiner*—Robert D. Budens
*Attorney, Agent, or Firm*—Jones & Askew, LLP

[57] ABSTRACT

The present invention relates to an immunotherapeutic agent that is effective in treating a variety of diseases in animals and humans. More particularly, the present invention is a preparation of a modified mycobacterial cell wall extract that does not contain oil, that is capable of stimulating the immune system of an animal or human in such a way as to cause the body to neutralize, abort or eliminate infections, tumors and other disorders.

19 Claims, No Drawings

IMMUNOSTIMULATORY BACTERIAL CELL WALL TRACTION

This a continuation of application Ser. No. 08/011,655, filed Jan. 29, 1993, now abandoned.

TECHNICAL FIELD

The present invention relates to an immunotherapeutic agent that is effective in treating a variety of diseases in animals and humans. More particularly, the present invention is a preparation of a modified mycobacterial cell wall extract that does not contain oil, that is capable of stimulating the immune system of an animal or human in such a way as to cause the body to neutralize, abort or eliminate infections, tumors and other disorders.

BACKGROUND OF THE INVENTION

Immunotherapy utilizing mycobacterial cell wall extracts has been extensively evaluated in animal tumor models, in patients suffering from cancer, and in treatments for infectious diseases. In active immunotherapy, various immunostimulants, immunorestorative agents, or tumor cell vaccines have been given directly to the tumor host with the idea of boosting endogenous resistance to tumor growth. A number of bacteria and bacterial products have been administered in an attempt to immunologically inhibit tumor growth. Extracts from bacille Calmette-Guerin (BCG), Corynebacterium species, *Corynebacterium parvum*, Mycobacterium species, Coryneform bacteria, Proprionebacterium acnes (*C. parvum*), Rhodococcus species, Eubacterium species, *Listeria monocytogenes*, Bordetella species and Nocardia species, among others, have been used in such studies. Success for immunotherapy with immunostimulants requires, in general, immunogenicity of the neoplasm, an optimal dose and schedule of administration of the immunostimulant, and direct contact between immunostimulant and tumor cells.

Intralesional injection of BCG with oil has been reported to produce regression of well established intradermal guinea pig hepatoma transplants with lymph node metastasis and can establish systemic tumor-specific immunity that can eliminate distant disease. In humans, direct intralesional injection of BCG with oil into melanomas has produced regression of injected nodules and, to a much lesser extent, regression of noninjected nodules. This therapy is complicated by severe flu-like systemic symptoms beginning within a few hours of injection and lasting about 24 hours. A late adverse effect is skin ulceration at the injection site. Intravesical administration of BCG has produced tumor regression of superficial bladder carcinomas.

Two components relevant to the proposed immunostimulant activity have been identified and isolated from the BCG complex. N-Acetyl-muramyl-alanyl-3-isoglutamine (muramyl dipeptide, or MDP) is a small component of the mycobacterial cell wall that can mediate the adjuvant activity produced by whole mycobacteria in the water-in-oil emulsion of Freund's complete adjuvant. MDP has been reported to activate macrophages and potentiate T- and B-cell-mediated reactions. Macrophages can be activated by phagocytosis of MDP encapsulated liposomes. In experimental tumor metastases, multiple injections of liposome encapsulated MDP has been reported to diminished the number of lung and lymph node metastases. Trehalose dimycolate (TDM), another component of mycobacteria that has adjuvant activity, has been reported to have antitumor activity in murine tumor models.

Other chemical substances have also undergone trials as agents to augment tumoricidal activities, among which have been pyran copolymer, and levamisole, an anthelmintic drug. Levamisole has had no apparent beneficial effect when used to treat human cancer.

Two general actions have been proposed for the local and regional effects of BCG and other bacterial products. Tumor cells may be killed as bystanders of severe inflammation evoked by the immunostimulant, or these same agents may act as adjuvants to enhance immunity against tumors. Contact with macrophages (activated directly by some bacterial products or indirectly through the production of mediators by T cells) is considered to be an important factor in tumor cell killing.

Whether large complex molecules like peptidoglycans or lipopolysaccharides or simple molecules such as muramyl dipeptide are used, the common pathway points to macrophage activation as the mechanism of adjuvant activity. The stimulation of macrophages by adjuvants results in increased antigen uptake, enhanced cytotoxicity, phagocytosis, hydrogen peroxide production, arachidonic acid metabolism, enzyme degranulation, and the synthesis and release of polypeptide monokines. The polypeptide monokines play an important role because they possess potent biological properties for various cells. To date, these monokines include interleukin 1, alpha interferon, tumor necrosis factor (cachectin), and colony-stimulating factors. Each monokine can, in turn, trigger other cells to produce biologically active cytokines.

In those studies which demonstrate activity by mycobacterial cell wall extracts, the extract must first be mixed with oil, usually as an emulsion, before administration to the subject. It is believed that the oil is required to effectively present the cell wall constituents to the proper cells in the immune system. However, presence of oil in the preparation greatly complicates the use of such preparations as therapeutic agents. The presence of oil in preparations of the mycobacterial cell wall extract has the potential for severe reactions at the site of the injection. In addition, the oil can cause granulomas to form. The severe reactivity caused by the oil in the cell wall preparation makes the preparation less acceptable as a therapeutic for humans.

Thus, what is needed is a mycobacterial cell wall extract that is capable of stimulating the immune system in a human or animal without the reactions caused by the presence of oil in the preparation. The preparation should have immunostimulating activity that is similar to that of mycobacterial cell wall extracts in an oil emulsion. Further, a cell wall extract without oil would allow the final product to be terminally sterilized, (autoclaved), yielding a sterile product.

SUMMARY OF THE INVENTION

The present invention solves the above problems by providing a suspension of a mycobacterial cell wall extract that can be administered to a human or animal without the presence of oil or oil-like substances, and that will cause the immune system of the human or animal to be generally stimulated. The mycobacterial cell wall extract is preferably extracted from Mycobacterium species including *Mycobacterium phlei*, Corynebacterium species and Nocardia species among others, are also a preferred source of mycobacterial cell wall extract. The stimulation of the immune system resulting from the above suspensions causes the human or animal to neutralize an infectious agent or retard the growth of cancer cells.

Administration of the mycobacterial cell wall extract of the present invention causes the immune system to be generally stimulated. For example, when a viral infection is aborted by use of the mycobacterial cell wall extract of the present invention, the signs and symptoms produced by viral replication and secondary bacterial infections are considerably reduced or eliminated because interruption of viral replication breaks the infective cycle.

The present invention comprises a suspension of a modified cell wall fraction in saline or other aqueous solution, without oil. The cell wall fraction may be extracted from bacille Calmette-Guerin (BCG), Corynebacterium species, *Corynebacterium parvum*, Mycobacterium species, Coryneform bacteria, Proprionebacterium acnes (*C. parvum*), Rhodococcus species, Eubacterium species, *Listeria monocytogenes*, Bordetella species and Nocardia species. Briefly, the bacteria are grown in liquid medium and harvested. The cell walls are prepared by disrupting the bacteria and then harvesting the disrupted bacteria by centrifugal sedimentation. The cell wall fraction (pellet from the centrifugation step) is then deproteinized by digestion with proteolytic enzymes. The resulting fraction is then treated with detergents and washed. The resulting insoluble fraction is then lyophilized. This fraction is suspended in an aqueous solution, such as saline, and injected into an animal or human to stimulate the immune system. It is an essential element of the present invention that the modified cell wall fraction is not adsorbed to or mixed with an oil fraction. It has been unexpectedly found that the modified cell wall fraction is highly effective without the use of oil in the preparation.

The resulting deproteinized cell wall fraction can be used to treat a wide variety of infections caused by any virus, bacteria, or intracellular organism including, but not limited to, infection by herpes virus such as equine rhinopneumonitis, infectious bovine rhinotracheitis, herpes simplex, herpes zoster, ocular herpes, feline viral rhinotracheitis, and a herpes virus which infects the respiratory tracts of cats. The invention also is effective as an aid in the treatment of parvovirus infections of young dogs. The mycobacterial cell wall extract of the present invention is efficacious as a therapeutic for genital herpes infections and acquired immune deficiency syndrome of humans, as well as other viral infections of animals and humans. The present invention is also effective in treating various cancers that occur in both humans and animals. The cancers can be primary or metastatic.

The aqueous suspension of mycobacterial cell wall extract of the present invention is different from conventional therapy in that the present invention nonspecifically causes the immune system to be activated, thereby providing protection against a wide variety of infections by microorganisms and cancers. Thus, the present invention is effective in treating infections in animals that are not immune to the infecting organism.

Accordingly, it is an object of the present invention to provide an aqueous suspension of mycobacterial cell wall extract that does not contain an oil fraction and is still effective in stimulating the immune system of a human or animal.

It is a further object of the present invention to provide an aqueous suspension of mycobacterial cell wall extract that does not contain an oil fraction that is effective in treating a wide variety of infections caused by microorganisms.

Another object of the present invention is to provide an aqueous suspension of mycobacterial cell wall extract that does not contain an oil fraction where the oil fraction can be toxic to the recipient.

Another object of the present invention is to provide an aqueous suspension of a mycobacterial cell wall extract that does not contain an oil fraction that does not sensitize the host to tuberculin skin tests.

Yet another object of the present invention is to provide an aqueous suspension of a mycobacterial cell wall extract that does not contain an oil fraction that is effective in treating tumors.

Another object of the present invention is to provide an aqueous suspension of a mycobacterial cell wall extract that does not contain an oil fraction, and that can be stored for a long period of time and remain effective.

Yet another object of the present invention is to provide an aqueous suspension of cell wall extract that does not contain an oil fraction and therefore has a lower risk of causing microembolism.

Another object of the present invention is to provide an aqueous suspension of cell wall extract that does not contain an oil fraction and is not known to cause granuloma oil emboli.

Another object of the present invention is to provide an aqueous suspension of a mycobacterial cell wall extract that does not contain an oil fraction that will not cause a reaction in the recipient.

Another object of the present invention is to restimulate the normal immune response following immunotolerance or immunosuppression.

Another object of the present invention is to provide a sterile product, free of oil, via terminal sterilization (autoclaving).

Another object of the present invention is to provide a mycobacterial cell wall extract preparation that will not cause a reaction at the site of administration.

Yet another object of the present invention is to provide an aqueous suspension of cell wall extract that does not contain an oil fraction, and does not cause severe reactions at the site of the injection.

Another object of the present invention is to provide an aqueous suspension of a mycobacterial cell wall extract that does not contain an oil fraction and will not cause a hypersensitivity response.

These and other objects, features and advantages of the present invention will become apparent after a review of the following detailed description of the disclosed embodiment and the appended claims.

DETAILED DESCRIPTION OF THE DISCLOSED EMBODIMENT

The present invention relates to an aqueous suspension of a mycobacterial cell wall extract that is effective in treating the immune system in animals and humans. The aqueous suspension can optionally have glycosaminoglycans, such as hyaluronic acid, as a component. The present invention is an aqueous preparation of modified bacterial cell walls that does not contain any oil or oil-like substances. Because there is no oil in the aqueous suspension of the mycobacterial cell wall extract that comprises the present invention, the unwanted side effects that are present in the cell wall preparations that are in the prior art are eliminated. The aqueous suspension of the mycobacterial cell wall extract is capable of stimulating the immune system of an animal or human, thereby causing the body to neutralize or abort an infection or retard or eliminate the growth of a cancer.

The present invention does not cause a positive tuberculin reaction in the recipient and rarely causes a hypersensitivity response upon repeated injection. The aqueous suspension of mycobacterial cell wall extract of the present invention can be used to treat a wide variety of disorders in humans or animals.

It is to be understood that the present invention is not an immunization process but is an agent that is capable of generally stimulating the immune system of an animal or human so that the individual's own immune system is capable of rapidly eliminating the disorder. Thus, the aqueous suspension of mycobacterial cell wall extract of the present invention is ideally suited for treatment of ongoing viral infections and is a novel immunotherapeutic agent in contrast to conventional prophylactic immunization.

The aqueous suspension of mycobacterial cell wall extract is useful for generally stimulating the immune system of the human or animal to which the suspension is administered. In particular, the present invention is useful in combating infectious diseases caused by microorganisms, especially viral infections. In addition, the present invention is useful in retarding or eliminating the growth of a wide variety of tumors including primary tumors and metastatic cancers. When treating primary tumors the aqueous mycobacterial cell wall extract can be injected directly into the tumor or it can be given systemically.

The present invention comprises an aqueous suspension of a modified bacterial cell wall preparation that does not contain any oil or oil-like substances. The aqueous suspension can optionally have glycosaminoglycans (GAG's) as a component. Examples include, but are not limited to polysulfated GAG's, and salts of hyaluronic acids including sodium hyaluronate. The preferred glycosaminoglycan is hyaluronic acid, which is of roostercomb or streptococcal origin. The hyaluronic acid derived from streptococcus has a molecular weight range of 300,000 to 2,000,000 daltons (D) and a preferred range of 500,000 to 1,200,000 D and a concentration range of 0.001% to 1.0% and a preferred range of 0.01% to 0.1%.

The preferred microorganism is the *Mycobacterium phlei*. However, any Mycobacterium species can be used to prepare the aqueous suspension of mycobacterial cell wall extract of the present invention. Other bacteria that can be used as a source of cell walls include, but are not limited to the following: bacille Calmette-Guerin (BCG), Corynebacterium species, *Corynebacterium parvum*, Mycobacterium species, Coryneform bacteria, Proprionebacterium acnes (*C. parvum*), Rhodococcus species, Eubacterium species, *Listeria monocytogenes*, Bordetella species and Nocardia species.

Basically, the present invention is prepared by growing the microorganism, *Mycobacterium phlei*, for example, in Bacto AC broth (Difco Labs, Detroit, Mich.) for 10 to 20 days after primary culture on Petragnani medium (Difco Labs, Detroit, Mich.) or in Lowenstein-Jensen medium (Difco Labs, Detroit, Mich.) for 10 to 20 days. The cells are harvested by centrifugal sedimentation and disrupted either under pressure or by sonic disruption. Disruption of bacteria means breaking the bacterial cell walls so that the soluble contents of the bacteria are released into the surrounding environment. The disrupted bacterial cells are collected by centrifugation and resuspended in distilled water. The cell/water suspension is first treated in a blender at high speed. The bacterial cells are further disrupted by sonication in a sonifier such as a Branson Sonifier 350 cell disrupter (Branson Sonic Power Co., Danbury, Conn.). The cells may also be disrupted in a high pressure cell fractionator such as a Ribi Cell Fractionator. This particular cell fractionator is no longer manufactured but is well known to one of ordinary skill in the art. The bacterial cells are placed in a chamber of a high pressure cell fractionator. The chamber is then pressurized to pressures greater than 30,000 pounds per square inch. The pressure is then rapidly released and the cells are disrupted by decompression.

The cell wall fraction is then washed and separated from any unbroken cells. The effluent or sonicate is transferred to centrifuge bottles and is spun at about 27,500×g for 1 hour at 15° C. in an intermediate speed centrifuge. After centrifugation, the supernatant solution is discarded and the sedimented crude cell wall fraction is transferred to a blender. It is important at this step to discard the undermost, white pellet of unbroken cells. The cell walls are suspended in deionized, sterile water and are washed by centrifugation. The washed cell wall fraction is resuspended in deionized, sterile water and spun at low speed (about 350 to 500×g) to remove any unbroken cells. After the low speed centrifugation, the cell wall fraction is pelleted from the supernatant solution by centrifugation at 27,500×g.

The crude cell wall fraction is then deproteinized by treating the cell walls with several proteinases. It is to be understood that many different proteinases, and even chemical extraction methods, can be used for this step in the cell wall modification process. The preferred method of deproteinating the cell walls is by sequential treatment of the cell wall fraction with trypsin and pronase. The crude cell wall fraction is resuspended in an aqueous buffered solution such as 0.05 M Tris-HCl, pH 7.5. Trypsin (pancreatic trypsin, Sigma Chemical Co., St. Louis, Mo.) is added, and the mixture is stirred at room temperature for 6 to 24 hours. After the trypsin treatment, pronase (*Streptomyces griseus* protease, Sigma Chemical Co., St. Louis, Mo.) is added and the suspension is allowed to incubate at room temperature for 6 to 24 hours.

The cell wall fraction is then optionally treated with detergent and phenol to extract any nucleic acids and/or lipids that may be present in the cell wall fraction. The preferred extraction mixture is urea, Triton X-I00, and phenol. For example, between about 40 to 80 g of urea, 0.5 to 4 ml of 100% Triton X-I00, and 50 to 150 g of phenol are added to each liter of deproteinized cell wall suspension. The suspension is then warmed to about 60° to 80° C. and stirred for 1 hour. After the heating step with the phenol and detergents, the suspension is spun for 10 minutes at about 16,000×g in capped bottles in an intermediate speed centrifuge in a GSA rotor. The supernatant solution is decanted and the dark phenol solution under the pellet is carefully removed. The cell wall pellet is washed several more times by centrifugation to remove any residual phenol.

Next the modified cell wall pellet is lyophilized, a process well known to one of ordinary skill in the art. The lyophilized cell wall pellet can be stored indefinitely at −20° C. in a desiccator jar.

Thimerosal (ethylmercurithiosalicylate, Sigma Chemical Co., St. Louis, Mo.) can optionally be added as a preservative. The preferred concentration of Thimerosal is about 0.1 g per liter. The Thimerosal and additional buffer are optionally added to the emulsified cell walls prior to the step of mixing at 60°–80° C. for one hour.

After the resuspension of the lyophilized cell wall extract in saline, the extract may be handled in one of two methods. First, the extract may be aseptically processed whereby vials are filled with the extract and sealed under aseptic conditions. In the alternative, the extract may be terminally sterilized (autoclaved) thereby avoiding the need for sterile conditions during the handling of the extract.

Preparations not containing oil may be terminally sterilized. Further, terminally sterilized preparations may be guaranteed to be sterile, whereas aseptically processed preparations cannot achieve that level of certainty, and may be contaminated. Therefore, a cell wall extract that does not contain oil has the further advantages that it can be guaranteed to be sterile, it is less costly, and it is less difficult to prepare.

In one embodiment of the present invention, the isolation of a mycobacterial cell wall (MCW) extract from *Mycobacterium phlei* is summarized as follows:
1. Cell Growth
   a. Identify seed culture as pure *Mycobacterium phlei*.
   b. Inoculate broth media in Erlemeyer flasks.
   c. Incubate 7–14 days at 36° C.
2. Concentration of whole cells
   a. Centrifugation.
3. Washing of whole cells.
   a. Repeated centrifugations in distilled water.
4. Inactivation and disruption of whole cells
   a. Branson Sonicator (or)
   b. Ribi Cell Fractionator.
5. Detoxification of disrupted cells
   a. Repeated centrifugations in deionized water.
6. Concentration of raw MCW
   a. Centrifugation.
7. Deproteinization of raw MCW
   a. Suspension in acid solution.
   b. Degradation in trypsin for 6–24 hours.
   c. Degradation in pronase for 6–24 hours.
   d. Incubation in urea/phenol for 1 hour.
8. Pasteurization at 60°–80° C. for 1 hour.
9. Concentration of deproteinized and purified MCW
   a. Centrifugation.
10. Stabilization
    a. Lyophilization
    b. Optionally add Thimerosal.
11. Resuspend in saline
    a. Aseptic filling (or)
    b. Terminal sterilization by autoclaving.

The present invention is used preferably by injecting a single dose of the agent intramuscularly. However, it should be understood that the present invention is effective when injected subcutaneously, intravenously, or when administered intratumorally, intravesically, topically or orally. For treating primary tumors, the aqueous suspension of mycobacterial cell wall extract can be injected directly into the tumor. For some disorders, more than one treatment may be desirable. The optimal dose of the aqueous suspension of mycobacterial cell wall extract of the present invention varies with the size of the animal or human that is being treated. Only an amount sufficient to stimulate the immune system is required. Normally a single dose is a suspension of from about 500 µg to 10 mg of cell wall per ml in a total volume of from about 0.25 to 5.0 ml. A preferred single dose is an emulsion of from about 300 µg to 6 mg of cell wall per ml. The most preferred single dose is an emulsion of from about 100µg to 2 mg of cell wall per ml in a total volume of from about 0.25 to 5.0 ml.

It is a critical aspect of the present invention that the aqueous suspension of mycobacterial cell wall extract does not contain any oil or oil-like substance. All of the prior art preparations of mycobacterial cell wall extracts known to the inventors contain an oil fraction or an oil-like fraction.

Unexpectedly, the mycobacterial cell wall extract made according to the present invention does not require oil for immune stimulating activity in a human or animal. The antiinfective or anticancer specific activity of the aqueous suspension of mycobacterial cell wall extract of the present invention is generally equal to or slightly less than the specific activity of the prior art water-in-oil preparations. However, it has been found that increasing the concentration of mycobacterial cell wall extract in the aqueous solution does not cause any unwanted side effects.

The following examples will serve to further illustrate the present invention without, at the same time, however, constituting any limitation thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE I

*Mycobacterium phlei* was obtained from the Institut fur Experimental Biologic and Medizin, Borstel, West Germany, and was stored as a suspension in sterile milk at –60° C. Approximately 11 transfers of the isolate were made between 1976 and 1985 without any diminution of immunostimulant activity of the modified cell walls. The *M. phlei* was cultured on Petragnani medium (Difco Labs, Detroit, Mich.).

EXAMPLE II

Bacterial cell walls were prepared with a Ribi Cell Fractionator. The Ribi cylinder, piston, and valve components were cleaned and assembled before each use. Approximately 400 grams of moist cell mass were placed into a clean blender with a capacity of approximately 1200 ml. The cell mass was mixed at high speed for between 30 to 60 seconds. After mixing, 6 ml of Tween 80 and between 200 and 400 ml of sterile water were added to the cell mixture. The entire cell suspension was then mixed in the blender at low speed for about 10 seconds. The cell suspension was refrigerated and remixed before each refill of the Ribi cylinder. The Ribi cylinder was filled with the cell suspension and processed in the fractionator at 33,000 pounds per square inch. The cylinder was then refilled and the procedure was repeated until the entire cell suspension had been processed. The effluent from the Ribi cylinder was stored in a sterile flask on ice during the fractionation process.

EXAMPLE III

The effluent from the fractionation procedure of Example II was transferred to 250 ml centrifuge bottles and spun for 1 hour at 27,500×g at 15° C. in an intermediate speed centrifuge with a GSA rotor. The supernatant fluid from the centrifugation was then decanted and discarded. The undermost, white pellet of unbroken cells was discarded. The sedimented crude cell wall fraction was transferred to a blender and suspended in sterile, deionized water by mixing at low speed. The crude cell wall fraction was washed by resuspension and centrifugation (27,500×g at 15° C. for one hour). Again, the undermost, white pellet of unbroken cells was discarded.

After washing the crude cell wall fraction, the pellet was resuspended in sterile, deionized water and spun for 5 minutes at 350×g to sediment unbroken cells while retaining the cell walls in the supernatant fluid. The supernatant fluid was then decanted and centrifuged at 27,500×g for 1 hour at 15° C. to sediment the crude cell wall fraction.

EXAMPLE IV

The crude cell wall fraction from Example III was then deproteinized by digestion with proteolytic enzymes. The crude cell wall fraction, derived from about 400 g of whole cells, was resuspended in 1 liter of 0.05 M Tris-HCl, pH 7.5, by mixing at low speed. After the crude cell wall fraction was thoroughly resuspended in the Tris buffer, 50 mg of trypsin (pancreatic trypsin, Sigma Chemical Co., St. Louis, Mo.) were added and stirred using a magnetic stirring bar at room temperature for 24 hours. Following the trypsin treatment, 50 mg of pronase (*Streptomyces griseus* protease, Sigma Chemical Co., St. Louis, Mo.) were added to each liter of trypsin digested cell wall suspension. The suspension was stirred using a magnetic stirring bar for 24 hours at room temperature.

EXAMPLE V

The protease digested cell wall fraction from Example IV was then treated with detergent and phenol. To each liter of cell wall suspension, 60 g of urea (J.T. Baker Chemical Co., Phillipsburg, N.J.), 2.0 ml of 100% Triton X100 (polyoxyethylene ethers, Sigma Chemical Co., St. Louis, Mo.), and 100 g of phenol crystals (Fisher Scientific, Fair Lawn, N.J.) were added. The flask containing the suspension was loosely covered with aluminum foil and warmed to 60°–80° C. and stirred for one hour. The deproteinized cell wall fraction was then spun for 10 minutes at 16,000×g in a GSA Rotor (Ivan Sorvall, Inc., Norwalk, Conn.). The supernatant fraction was decanted and discarded and the dark fluid beneath the pellet was removed using a disposable pipette. The cell wall pellet was washed three times by resuspending it in about one liter of sterile water, and centrifuged at 16,000×g for 10 minutes in a GSA rotor.

EXAMPLE VI

The washed, modified cell wall pellet was then lyophilized by transferring the suspension to a lyophilizing flask with a small amount of deionized sterile water. One 300 ml lyophilizing flask was used for each 30 grams of wet cell wall starting material. The cell wall suspension was shell frozen by rotating the flask in ethanol that had been cooled with solid carbon dioxide. After the content of the flask was frozen, the flask was attached to a lyophilization apparatus (Virtis Co., Inc., Gardiner, N.Y.). After the sample was lyophilized, it was transferred to a sterile, screw-cap container. The material was stored at −12° C. in a desiccator jar containing anhydrous calcium sulfate.

EXAMPLE VII

To test the potency of the cell wall preparation that does not contain oil, a mouse splenomegaly potency test is performed. Female CD1 mice which are between the ages of seven and eight weeks and between the weights of 20 g and 30 g are used to perform the test. The animals are randomized and then separated into eleven groups of 20 animals. The mice are housed 5 per cage. Food and water are supplied ad lib. The final concentration of mycobacterial cell wall extract from Example VI is 400 µg/ml. Immediately prior to injection of the test material, three ml of the final product is diluted in 4.5 ml of PBS or PBS-D. The formulation of PBS-D is as follows: 16.5 ml of 0.2 M $NaH_2PO_4$, 33.5 ml of 0.2 M $Na_2HPO_4$, 7.4 g of NaCl, and using water, dilute to the final volume of one liter.

Animals are placed in dorsal recumbency with the head directed downward, and 0.5 ml of the test material is injected intraperitoneally using a 27 gauge ½inch needle.

Twenty mice are injected with the test material composition (0.5 ml of 400 µg/ml) and another 20 control mice are injected with 0.5 ml of saline (PBS). Also, the other groups of 20 mice are injected with 0.5 ml of one of the other test materials shown in Table I. Any abnormalities (anorexia, distress, huddling, rough coats or deaths) are recorded on a daily basis.

The formulation of the oil-in-water suspension (emulsion control) per 1000 ml is as follows: 1000 µg mycobacterial cell wall extract (MCWE), 2% mineral oil, 100 mg/L Thimerosal, and 975 PBS-D. All suspensions are mixed well before injection.

All animals are sacrificed by cervical dislocation or carbon dioxide intoxication after 7 days, and body weights are determined. Immediately after euthanasia, a midline incision is made and the abdominal wall is folded back to expose the internal viscera. The peritoneum is incised and the intestines and surrounding organs are moved away from the spleen. The spleen is extracted ensuring that there is no inclusion of extraneous tissue. The individual spleens are immediately weighed using a balance with the sensitivity of at least 0.001 g.

The spleen to body weight relationship is determined by converting the spleen weight of each animal to mg spleen/ 100 g of body weight by the following formula:

$$\frac{\text{Spleen weight (mg)} \times 100}{\text{Weight of animal (g)}}$$

The spleen weight (mg)/100 g body weight for each of the control and test group is averaged. The average spleen weight of the control group to the average spleen weight of the test product is compared by analysis of variance (ANOVA). A statistical significance of p<0.01 is considered a positive potency test.

TABLE I

| Test Material | Avg Spl/B wt | Avg. Spl wt | P-value vs PBS | P-value (vs HA) | P-value vs MCWE & oil |
|---|---|---|---|---|---|
| Saline (PBS) control | 369.920 | 99.630 | — | .91 | — |
| HA alone control | 374.335 | 91.000 | .9139 | — | — |
| Emulsion Control | 425.567 | 108.500 | 0.0633 | — | — |
| MCWE[a] in saline | 539.377 | 134.100 | .00034 | — | .1254 |
| MCWE (23E)[b] | 633.980 | 167.850 | .000025 | .00013 | — |
| 1 mg HA[c]/1000 µg MCWE | 651.784 | 154.700 | .0013 | .0016 | .8242 |
| 1 mg HA/1500 µg MCWE | 606.616 | 144.200 | .0027 | .0027 | .7272 |
| 1 mg HA/2000 µg MCWE | 713.030 | 165.300 | .0018 | .0019 | .3657 |
| 0.1 mg HA/1000 µg MCWE | 685.213 | 171.900 | .00072 | .00033 | .6253 |
| 0.1 mg HA/1500 µg MCWE | 552.600 | 140.900 | .0458 | .0567 | .349 |
| 0.1 mg HA/2000 µg MCWE | 574.894 | 151.400 | .0066 | .0076 | .4529 |

[a]MCWE = mycobacterial cell wall extract as described in Examples I–IV.
[b]23E = Production Serial No. Lot 921123E of positive control; regular MCWE oil-in-water suspension.
[c]HA = hyaluronic acid derived from roostercomb or *streptococcus*.

As shown in Table I, the mycobacterial cell wall extract without oil is nearly as effective as the conventional oil-in-water emulsion mycobacterial cell wall extract preparation.

It should be understood, of course, that the foregoing relates only to preferred embodiments of the present invention and that numerous modifications or alterations may be made therein without departing from the spirit and the scope of the invention as set forth in the appended claims.

What is claimed is:

1. A method of stimulating the immune system in a human or animal comprising administering to the human or animal an effective amount of an aqueous suspension of an insoluble bacterial cell wall fraction that does not contain oil, wherein said cell wall fraction is treated to extract lipids from the fraction, and wherein the insoluble cell wall fraction is prepared from *Mycobacterium phlei*.

2. The method of claim 1, wherein the effective amount is from about 500 μg of cell wall fraction per 0.25 ml of suspension to about 10 mg of cell wall fraction per 5.0 ml of suspension in a total volume of from about 0.25 to 5.0 ml.

3. The method of claim 1, wherein the effective amount is from about 300 μg of cell wall fraction per 1 ml of suspension to about 6 mg of cell wall fraction per 1 ml of suspension in a total volume of from about 0.25 to 5.0 ml.

4. The method of claim 1, wherein the effective amount is from about 100 μg of cell wall fraction per 1 ml of suspension to about 2 mg of cell wall fraction per 1 ml of suspension in a total volume of from about 0.25 to 5.0 ml.

5. A method of stimulating the immune system in a human or animal comprising administering to the human or animal an effective amount of an aqueous suspension of an insoluble bacterial cell wall fraction that does not contain oil, wherein said cell wall fraction is treated to extract lipids from the fraction, and wherein the insoluble cell wall fraction is prepared from *Rhodococcus equi*.

6. The method of claim 5, wherein the effective amount is from about 500 μg of cell wall fraction per 0.25 ml of suspension to about 10 mg of cell wall fraction per 5.0 ml of suspension in a total volume of from about 0.25 to 5.0 ml.

7. The method of claim 5, wherein the effective amount is from about 300 μg of cell wall fraction per 1 ml of suspension to about 6 mg of cell wall fraction per 1 ml of suspension in a total volume of from about 0.25 to 5.0 ml.

8. The method of claim 5, wherein the effective amount is from about 100 μg of cell wall fraction per 1 ml of suspension to about 2 mg of cell wall fraction per 1 ml of suspension in a total volume of from about 0.25 to 5.0 ml.

9. An immune stimulating composition comprising an aqueous suspension of an insoluble bacterial cell wall fraction that does not contain oil, wherein said bacterial cell wall fraction is treated to extract lipids from the fraction, and wherein the insoluble cell wall fraction is prepared from *Mycobacterium phlei*.

10. The composition of claim 9, wherein the composition is terminally sterilized by heat sterilization.

11. An immune stimulating composition comprising an aqueous suspension of an insoluble bacterial cell wall fraction that does not contain oil, wherein said bacterial cell wall fraction is treated to extract lipids from the fraction, and wherein the insoluble cell wall fraction is prepared from *Rhodococcus equi*.

12. The composition of claim 11, wherein the composition is terminally sterilized by heat sterilization.

13. An immune stimulating composition comprising an insoluble cell wall fraction prepared from bacterial cells having cell walls by a method comprising:

a) disrupting the bacterial cells to break the bacterial cell walls into fragments and to release the soluble contents of the bacterial cells;

b) separating the unbroken bacterial cells and soluble contents of the bacterial cells from the cell wall fragments to create a cell wall fraction;

c) deproteinizing the cell wall fraction; and d) treating the cell wall fraction to extract lipids from the cell wall fraction, wherein the bacterial cells are *Mycobacterium phlei* or *Rhodococcus equi* bacterial cells.

14. The composition of claim 13 wherein the preparation method further comprises separating the cell wall fraction from the extract.

15. The composition of claim 13 wherein the preparation method further comprises treating the cell wall fraction in step d with a preservative.

16. The composition of claim 13 wherein the preparation method further comprises lyophilizing the cell wall fraction.

17. The composition of claim 16 wherein the preparation method further comprises resuspending the lyophilized cell wall fraction in an aqueous solution.

18. The composition of claim 17 wherein the aqueous solution is saline.

19. The composition of claim 17 wherein the preparation method further comprises terminally sterilizing the resuspended fraction by heat sterilization.

* * * * *